(12) United States Patent
Ansari et al.

(10) Patent No.: US 11,948,670 B1
(45) Date of Patent: *Apr. 2, 2024

(54) SYSTEM AND METHOD FOR AUTOMATING PHARMACY PROCESSING OF ELECTRONIC PRESCRIPTIONS

(71) Applicant: WALGREEN CO., Deerfield, IL (US)

(72) Inventors: Mohsin Ovais Ansari, Highland Park, IL (US); Jill M. Kunicki, Salem, WI (US); Paul K. Wilson, Lake Villa, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/862,931

(22) Filed: Jul. 12, 2022

Related U.S. Application Data

(63) Continuation of application No. 16/383,792, filed on Apr. 15, 2019, which is a continuation of application
(Continued)

(51) Int. Cl.
*G16H 20/10* (2018.01)
*G06Q 10/10* (2023.01)

(52) U.S. Cl.
CPC ............. *G16H 20/10* (2018.01); *G06Q 10/10* (2013.01)

(58) Field of Classification Search
CPC ............................... G16H 20/10; G16H 10/10
(Continued)

(56) References Cited

U.S. PATENT DOCUMENTS 6,421,650 B1  7/2002 Goetz et al.
8,595,206 B1  11/2013 Ansari et al.
(Continued)

FOREIGN PATENT DOCUMENTS

JP   2009531779 A  *  9/2009
JP   2009531779 A     9/2009

OTHER PUBLICATIONS

Swartz, Nikki; A prescription for electronic health records: converting paper files into electronic health records (EHRs) ; Information Management Journal 38.4: 20(6). Association of Records Managers & Administrators (ARMA). (Jul. 2004-Aug. 2004) (Year: 2004).*
(Continued)

*Primary Examiner* — Hiep V Nguyen
(74) *Attorney, Agent, or Firm* — MARSHALL, GERSTEIN & BORUN LLP; Randall G. Rueth (57) ABSTRACT

A method and system may provide an automated pharmacy processing system which automatically processes an electronic prescription by converting the electronic prescription into a pharmacy prescription record. In this way, an electronic prescription can be filled by a pharmacist without manual data entry. The system receives an electronic prescription and compares data from the electronic prescription with entries in one or more pharmacy database(s). When there is a match between the electronic prescription data and an entry in the one or more pharmacy database(s), the system populates the pharmacy prescription record with data from the matching pharmacy database entry. If all of the data fields from the pharmacy prescription record have been populated the pharmacist can fill the electronic prescription.

20 Claims, 6 Drawing Sheets

Related U.S. Application Data

No. 14/192,780, filed on Feb. 27, 2014, now Pat. No. 10,311,536.

(58) Field of Classification Search
USPC .............................................. 705/3
See application file for complete search history.

(56) References Cited

U.S. PATENT DOCUMENTS

| 8,660,859 | B1 | 2/2014 | Ansari et al. | |
|---|---|---|---|---|
| 2002/0169635 | A1 | 11/2002 | Shillingburg | |
| 2005/0182656 | A1 | 8/2005 | Morey | |
| 2006/0235881 | A1* | 10/2006 | Masarie | G16H 20/10 |
| 2008/0017714 | A1 | 1/2008 | Melick et al. | |
| 2008/0177787 | A1* | 7/2008 | Karamchedu | G06Q 10/10 |
| 2008/0275738 | A1* | 11/2008 | Shillingburg | G16H 20/13 |
| | | | | 705/3 |
| 2013/0096938 | A1 | 4/2013 | Stueckemann et al. | |
| 2013/0304500 | A1 | 11/2013 | Tripoli | |

OTHER PUBLICATIONS

Ansari et al., U.S. Appl. No. 14/055,584, entitled "Methods and Systems of Correlating Electronic Pharmacy Data and Electronic Medical Records," filed Oct. 16, 2013.

Ansari et al., U.S. Appl. No. 14/147,822, entitled "Systems and Methods for Executing an Electronic Pharmacy Program That Requires Access to an Electronic Medical Record," filed Jan. 6, 2014.

Pulver et al.; "An Exploration of Ambulatory Prescription and Community Pharmacy Fulfillment Data for Improvement of Electronic Processes"; University of Colorado Denver, Anschutz Medical Campus; ProQuest Dissertations Publishing, 2015.

* cited by examiner

200 Patient Database

| Patient ID# | Patient Name | Patient Birth Date | Patient Address | Phone # | Insurance | Allergies |
|---|---|---|---|---|---|---|
| 123-46-6975 | Bob Johnson | 8/02/1974 | 123 Main St. | 312-555-5678 | State Farm | N |
| 216-64-5555 | John Smith | 3/05/1939 | 111 State St. | 312-555-1234 | All State | N |
| 675-41-2739 | Chris Bryant | 6/10/1992 | 555 N. Michigan | 312-555-1111 | Blue Cross | N |

300 Prescriber Database

| Prescriber ID# | Prescriber Name | Practice Name | Prescriber Address | DEA # | Phone # |
|---|---|---|---|---|---|
| 111111111 | John Doe | Doc & Assocs. | 312 S. Well St. | AA5555555 | 312-123-4567 |
| 222222222 | Bill Smith | Smith Offices | 12 N. Michigan | AA6666666 | 312-111-2222 |

400 Medication Database

| Medication Name | Size | Generic Equivalent | Controlled Substance |
|---|---|---|---|
| Prozac | 40 mg | Fluoxetine hcl | N |
| Prozac | 10 mg | Fluoxetine hcl | N |

SYSTEM AND METHOD FOR AUTOMATING PHARMACY PROCESSING OF ELECTRONIC PRESCRIPTIONS

CROSS REFERENCE TO RELATED APPLICATION

The present application is a continuation of U.S. patent application Ser. No. 16/383,792, entitled SYSTEM AND METHOD FOR AUTOMATING PHARMACY PROCESSING OF ELECTRONIC PRESCRIPTIONS, filed Apr. 15, 2019, which is a continuation of U.S. patent application Ser. No. 14/192,780, entitled SYSTEM AND METHOD FOR AUTOMATING PHARMACY PROCESSING OF ELECTRONIC PRESCRIPTIONS, filed Feb. 27, 2014, the disclosures of which are incorporated herein in their entireties by reference.

TECHNICAL FIELD

The present disclosure generally relates to a system and method for automating pharmacy processing of electronic prescriptions, and more particularly to fully generating pharmacy prescription records based on data from electronic prescriptions, in an efficient and expeditious manner.

BACKGROUND

Health care costs have been increasing at a fast rate. In an attempt to reform health care, legislation in the United States that includes incentivizing payors and providers to cooperate has been passed. As such, health providers are changing their approaches to providing health care to patients. Coordination of health care across multiple health care providers or health care organizations may not only decrease the cost of health care to payors, but may also improve the quality of health care to patients. Health care organizations may include pharmacy entities or enterprises that fill or provide prescription products and services, hospitals, health care data repositories, managed care organizations, physicians and/or physician groups, and other medical professionals that are licensed to prescribe medical products and medicaments to patients.

As a result, electronic prescriptions written by a physician are becoming increasingly more popular. However, electronic prescriptions from a physician are organized in a different format than the pharmacy prescription data necessary for a pharmacist to fill a prescription. Additionally, there are many variations of electronic prescriptions which have different data fields, some providing more detail than others and also which are organized in a variety of ways. The systems currently in place require a technician to read the electronic prescription and manually enter data from the electronic prescription into pharmacy prescription data fields. Once the technician has entered the data from the electronic prescription the pharmacist can fill the prescription. This manual process can be time consuming, leads to additional work for the technician and increases the likelihood of errors in the pharmacy prescription data.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

A "health care organization," as used herein, refers to a health care related enterprise or health care provider. The health care organization may be for profit or not-for-profit.

The health care organization may provide health care diagnostic, therapeutic, rehabilitation, and other services to patients. For example, the health care organization may provide physician care, therapy, imaging, counseling, or the like. The health care organization may provide inpatient and/or outpatient services, may include one or more physical locations or facilities. Additionally or alternatively, the health care organization may provide other health-care related services, such as providing billing management, providing health care insurance, maintaining electronic medical records, etc. Examples of health care organizations may include a hospital group, a medical practice group, an insurance group, a stand-alone imaging facility, a home-health service provider, and others. In some embodiments, a health care organization may include a pharmacy enterprise.

As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "patient" is used primarily so as to avoid confusion.

Generally speaking, an automated pharmacy processing system (also referred to herein as "the system") receives an electronic prescription from a health care organization using electronic medical records (EMRs), electronic health records (EHRs), or standalone e-Prescribing systems. The system automatically converts the information from the electronic prescription into a pharmacy prescription record, which can be filled by a pharmacist at a selected pharmacy location, without requiring a technician to manually enter data from the electronic prescription into the pharmacy processing system. The automated pharmacy processing system may convert patient identification information, prescribing physician (also referred to herein as a "prescriber") identification information, medication information, drug quantity, drug days' supply and prescriber instructions (SIG) from an electronic prescription format into the pharmacy prescription record. In addition, the automated pharmacy processing system may determine whether generic substitution of a brand name medication is allowed and substitutes the generic for the brand name medication on the electronic prescription.

Figure 1:
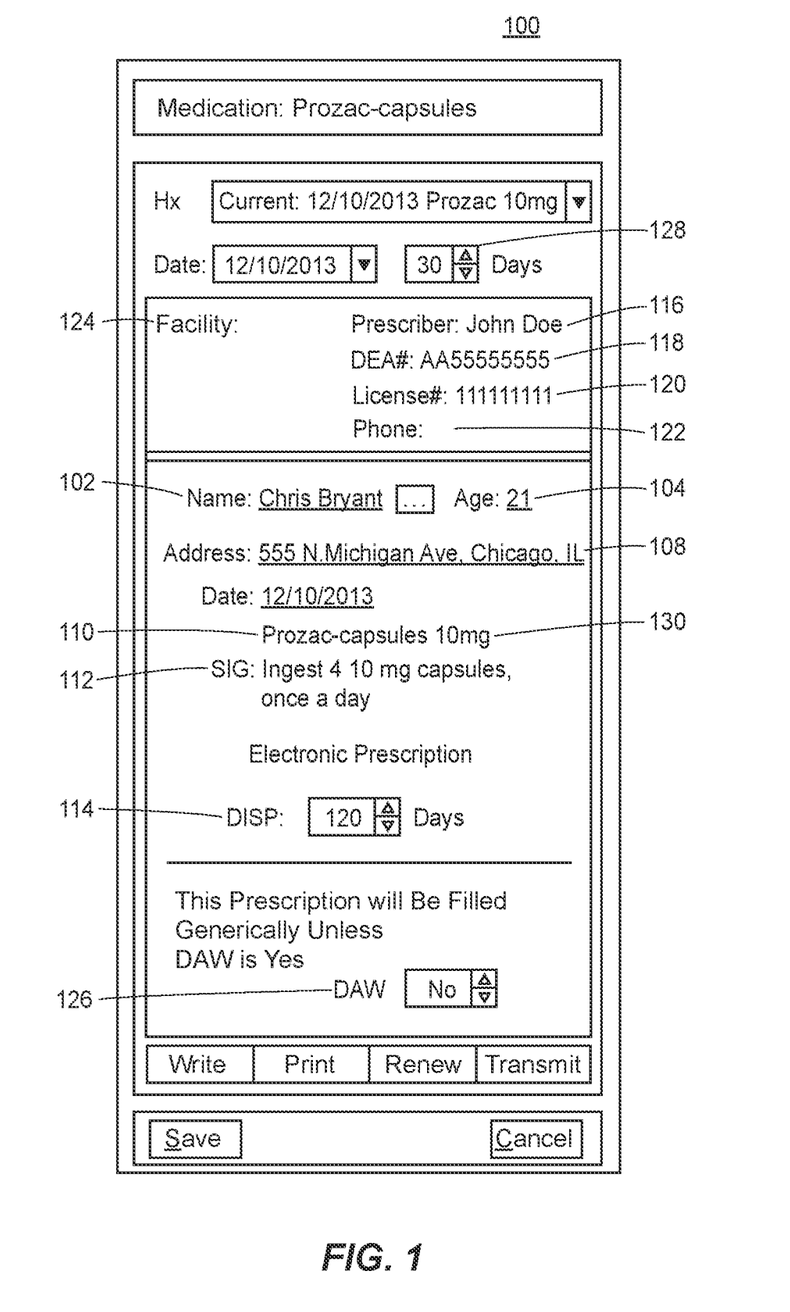
FIG. 1 depicts an exemplary electronic prescription which may be received by the automated pharmacy processing system.

Although the automated pharmacy processing system receives the electronic prescriptions via a digital network, the format in which the information or data is stored in an electronic prescription is different from the format in which pharmacy prescription data or records are stored. Therefore, it may be necessary to convert the data in an electronic prescription into a pharmacy prescription record format. To demonstrate the difference in formatting, FIG. 1 illustrates an exemplary electronic prescription for a particular patient. However, this is merely an example and electronic prescriptions may be formatted in any suitable number of ways. In the example of FIG. 1, the electronic prescription 100 includes several data fields which may be grouped into multiple prescription components for the automated pharmacy processing system. The prescription components include patient information, prescriber information, medication name information, quantity and days' supply and prescriber instructions.

For example, a patient name field 102, a patient age field 104, and a patient address field 108 may fit within the patient information component. On the other hand, a prescriber name field 116, a DEA number field 118, a prescriber license number field 120, a prescriber phone number field 122, and a prescriber facility field 124 may fit within the prescriber information component. Electronic prescription data which may fit within the medication name information component includes a medication name 110, a medication size 130 and a dispense as written (DAW) field 126 which is used to determine whether a generic substitute is permitted. Additionally, a number of days field 128 and a dispense (DISP) field 114 may fit within the days' supply and quantity components, respectively, while a prescriber instructions (SIG) field 112 may fit within the prescriber instructions component. The electronic prescription 100 may also include an indication of a pharmacy location for the patient to pick up the prescription. Alternatively, the pharmacy location may default to the closest location to the patient address 108.

In one embodiment, the automated pharmacy processing system may detect data by parsing the electronic prescription 100 to find field identifiers and XML tags corresponding to data fields. For example, the electronic prescription 100 may follow the SCRIPT standard defined and maintained by the National Council for Prescription Drug Programs (NCPDP), which defines field identifiers and XML tags for each data field. For example, the system may parse the electronic prescription 100 for an XML tag or field identifier indicating a DEA number field. However, this is merely one example of how data within an electronic prescription may be detected and categorized by the automated pharmacy processing system. Alternatively, data may be detected and categorized in any suitable number of ways and in some implementations data from the electronic prescription may not be categorized. For ease of illustration only, this application will continue to describe detecting data from an electronic prescription in the manner described above.

Figure 2:
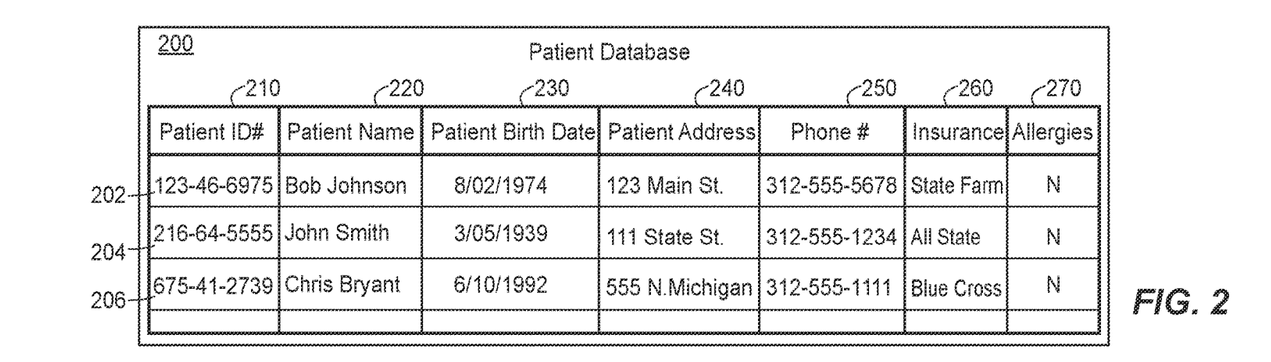
FIG. 2 depicts an exemplary portion of a pharmacy patient database which may be utilized in creating a pharmacy prescription record.
Figure 3:
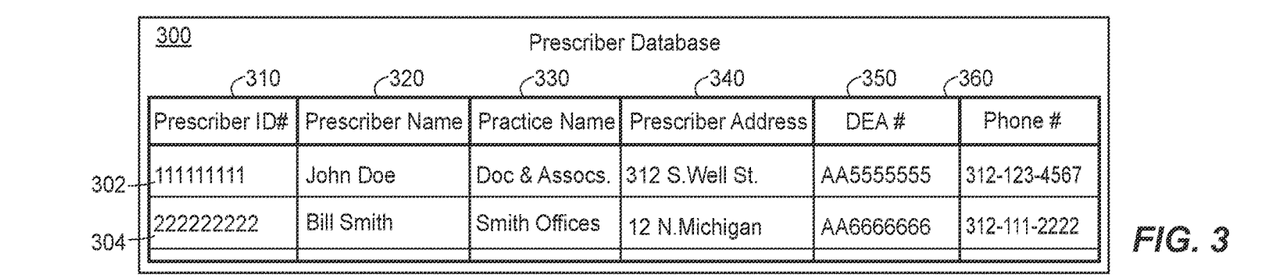
FIG. 3 depicts an exemplary portion of a pharmacy prescriber database which may be utilized in creating a pharmacy prescription record.
Figure 4:
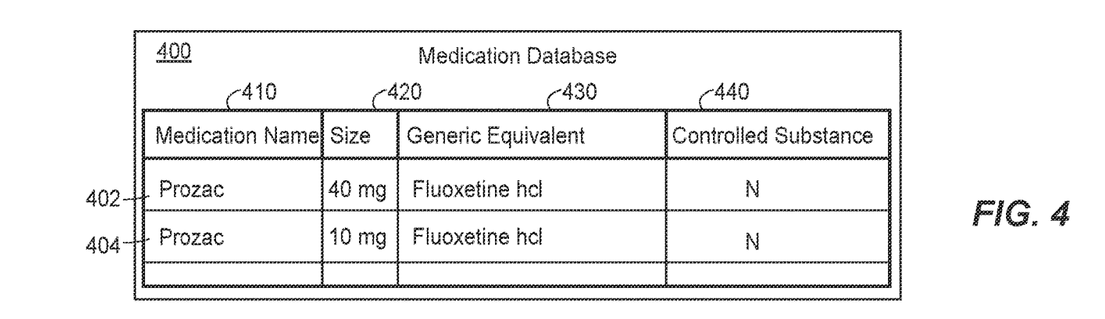
FIG. 4 depicts an exemplary portion of a pharmacy medication database which may be utilized in creating a pharmacy prescription record.

Once the automated pharmacy processing system detects data from the electronic prescription, the data is compared to one or more pharmacy database(s) illustrated in FIGS. 2-4. The one or more pharmacy database(s) illustrated in FIGS. 2-4 may be one database or a group of two or more databases. Each figure corresponds to one of the prescription components mentioned above.

Although FIGS. 2-4 depict the one more pharmacy database(s) as including only a few data entries, it should be understood that several data entries may be utilized. For example, the one or more pharmacy database(s) may include thousands of data entries. However, for ease of illustration only, merely a portion of the one or more pharmacy database(s) is illustrated in FIGS. 2-4.

FIG. 2 illustrates a portion of a pharmacy patient database 200 corresponding to the patient information component. Once the automated pharmacy processing system detects the data in the electronic prescription associated with patient information, the system compares the data from the electronic prescription to the data stored in the pharmacy patient database 200. Data in the pharmacy patient database 200 may include a patient identification number 210 such as a Medical Record Number (MRN), a patient name 220, a patient birth date 230, a patient address 240, a patient phone number 250, an insurance provider 260 along with other insurance information, and a list of allergies 270. However, this is just an example and additional or alternative data may also be stored in the pharmacy patient database 200.

In any event, data which is detected from the electronic prescription is compared to the data entries in the pharmacy patient database 200 to find a match. If the data detected from the electronic prescription as patient information is the same as one row of data fields (also referred to herein as an "entry") in the pharmacy patient database 200 then a match is generated, and the automated pharmacy processing system places the data corresponding to the matching entry in the pharmacy patient database 200 into a pharmacy prescription record. In an embodiment, if one data field from the electronic prescription matches with one data field of an entry in the pharmacy patient database 200, such as the patient identification number, then a match is generated for the entry. In other embodiments, more than one data field of the electronic prescription may need to be the same as more than one data field of an entry in the pharmacy patient database 200 to generate a match. In some embodiments the automated pharmacy processing system places only some of the data corresponding to the matching entry into the pharmacy prescription record.

For example, with reference to FIG. 1, the automated pharmacy processing system detects patient name 102 as "Chris Bryant," patient address 108 as "555 N. Michigan Avenue, Chicago, IL" and patient age 104 as "21." The system then looks up information in the pharmacy patient database 200 to find a matching entry. Because the automated pharmacy processing system does not detect a patient identification number in the electronic prescription 100, the system skips the first column 210 and detects whether the patient name 220 in entry 202 is the same as the patient name detected in the electronic prescription 100. However, the names do not match and the system proceeds to the next entry until it finds an identical name in entry 206 "Chris Bryant." The system may then proceed to check whether other data fields in entry 206 are also the same as the data detected in the electronic prescription, because there may be multiple patients named "Chris Bryant" in the pharmacy patient database 200. After comparing the patient information from the electronic prescription to an entry 206 in the pharmacy patient database, the automated pharmacy processing system determines whether to generate a match.

If the system determines there is a match, then information from the matching entry is used to populate the pharmacy prescription record. However, if the system determines there is no match, because the pharmacy patient database 200 does not store information similar to the detected patient information from the electronic prescription 100, then the system generates a new entry into the pharmacy patient database 200 using the detected patient information and populates the pharmacy prescription record with the new entry. On the other hand, if the system determines there are multiple matches, because the system cannot distinguish the detected patient information from multiple entries of the pharmacy patient database 200, the system requires manual entry into the pharmacy prescription record.

FIG. 3 illustrates a portion of a pharmacy prescriber database 300 corresponding to the prescriber information component. Once the automated pharmacy processing system detects the data in the electronic prescription associated with prescriber information, the system compares the data from the electronic prescription to the data stored in the pharmacy prescriber database 300. Data in the pharmacy prescriber database 300 may include a prescriber identification number 310 such as a National Provider Identifier (NPI) or a prescriber license number, a prescriber name 320, a practice name 330, a prescriber address 340, a DEA number 350, and a prescriber phone number 360. However, this is just an example and additional or alternative data may also be stored in the pharmacy prescriber database 300.

In any event, data which is detected from the electronic prescription is compared to the data entries in the pharmacy prescriber database 300 to find a match. If the data detected from the electronic prescription as prescriber information is the same as one entry or row of data fields in the pharmacy prescriber database 300 then a match is generated, and the automated pharmacy processing system places the data corresponding to the matching entry in the pharmacy prescriber database 300 into a pharmacy prescription record. In an embodiment, if one data field from the electronic prescription matches with one data field of an entry in the pharmacy prescriber database 300, such as the prescriber identification number, then a match is generated. In other embodiments, more than one data field of the electronic prescription may need to be the same as more than one data field of an entry in the pharmacy prescriber database 300 to generate a match. In some embodiments the automated pharmacy processing system places only some of the data corresponding to the matching entry into the pharmacy prescription record.

For example, with reference to FIG. 1, the automated pharmacy processing system detects prescriber name 116 as "John Doe," DEA number 118 as "AA5555555" and license number 120 as "111111111." Other prescriber information fields such as prescriber phone number 122 and prescriber facility 124 are left blank.

The system then looks up information in the pharmacy prescriber database 300 to find a matching entry. The same prescriber identification number 310 is found at entry 302 "111111111." At this point, the system may determine the information is the same and generates a match, because each prescriber has a unique identification number (National Provider Identifier (NPI) and/or other identifiers) and therefore duplicates do not exist. However, the system may compare the other data fields of entry 302 to make sure an error does not exist in either the pharmacy prescriber database 300 or the detected prescriber information of the electronic prescription 100. In this case, the system determines the prescriber name 320 in entry 302 "John Doe" is also the same as the prescriber name 116 in the electronic prescription 100.

If the system determines there is a match, then information from the matching entry is used to populate the pharmacy prescription record. However, if the system determines there is no match or there are multiple matches, the system requires manual entry into the pharmacy prescription record. The system determines there is no match when the pharmacy prescriber database 300 does not store information similar to the detected prescriber information from the electronic prescription 100. Multiple matches occur when the system cannot distinguish the detected prescriber information from multiple entries of the pharmacy prescriber database 300.

In addition to comparing prescriber information, FIG. 4 illustrates a portion of a pharmacy medication database 400 corresponding to the medication information component. Once the automated pharmacy processing system detects the data in the electronic prescription associated with medication information, the system compares the data from the electronic prescription 100 to the data stored in the pharmacy medication database 400. Data in the pharmacy medication database 400 may include a medication name 410, a medication size 420, a generic equivalent 430, and whether the medication is a controlled substance 440. The pharmacy medication database may also include a DAW code (not shown) and an NDC code (not shown). However, this is just an example and additional or alternative data may also be stored in the pharmacy medication database 400.

In any event, data which is detected from the electronic prescription is compared to the data entries in the pharmacy medication database 400 to find a match. If the data detected from the electronic prescription as medication information is the same as one entry or row of data fields in the pharmacy medication database 400 then a match is generated. In an embodiment, if one data field from the electronic prescription matches with one data field of an entry in the pharmacy medication database 400, such as the NDC code, then a match is generated. In other embodiments, more than one data field of the electronic prescription may need to be the same as more than one data field of an entry in the pharmacy medication database 400 to generate a match. If data detected from the electronic prescription indicates that generic substitution is permitted, then the automated pharmacy processing system places the data corresponding to the matching entry in the pharmacy medication database 400, including the generic equivalent but not the medication name, into a pharmacy prescription record. In the event there are multiple manufacturers for the generic drug, the automated pharmacy processing system checks the inventory system or modules to determine the exact generic product to dispense. On the other hand, if there is no indication from the electronic prescription data that generic substitution is permitted, the automated pharmacy processing system places the medication name into the pharmacy prescription record but does not place the generic equivalent.

For example, with reference to FIG. 1, the automated pharmacy processing system detects the medication name 110 as "Prozac," the medication size 130 as "10 milligrams," and DAW 126 as "No" meaning generic substitute is permitted.

The system then looks up information in the pharmacy medication database 400 to find a matching entry. The same medication name 410 is found at entry 402 "Prozac." The system may then compare the medication size 420 of entry 402 to the medication size detected in the electronic prescription. Here, the system determines the sizes are different and proceeds to entry 404 where both the medication name and the medication size is the same as in the electronic prescription.

If the system determines there is a match, then information from the matching entry is used to populate the pharmacy prescription record. However, if the system determines there is no match or there are multiple matches, the system requires manual entry into the pharmacy prescription record. The system determines there is no match when the pharmacy medication database 400 does not store information similar to the detected medication information from the electronic prescription 100. Multiple matches occur when the system cannot distinguish the detected medication information from multiple entries of the pharmacy medication database 400.

For example, the system places the entry 404 into the pharmacy prescription record, excluding the medication name Prozac but including the generic equivalent Fluoxetine HCL, because the system detects DAW 126 "No" in the electronic prescription 100 and determines generic substitution is permitted.

The automated pharmacy processing system also detects a quantity and a days' supply from the electronic prescription. With reference to FIG. 1, the system detects the quantity as "120" in the dispense field 114 and the days' supply as "30" in the days field 128. The detected quantity and days' supply are then used to populate the pharmacy prescription record. In addition, the automated pharmacy processing system detects prescriber instructions and translates the instructions into a data field of the pharmacy prescription record. For example, the automated pharmacy processing system may include a stored list of predetermined prescriber instruction components which can be combined together and then placed into the pharmacy prescription record. The prescriber instructions from the electronic prescription may be parsed to determine individual components and then translated into a combination of predetermined prescriber instruction components from the stored list. Predetermined prescriber instruction components may include an action, dosage, frequency, route of administration, etc.

For example, with reference to FIG. 1, the automated pharmacy processing system detects prescriber instructions in the SIG field 112 of the electronic prescription 100, which state "Ingest 4 10 mg capsules, once a day." The system may then translate the action component, "Ingest" to "Take" which corresponds to one of the predetermined prescriber instruction components in the stored list. Moreover, the system may translate the dosage component "4 10 mg capsules" to "4 10 mg capsules." The system may also translate the frequency component "once a day" to "daily" and combine the translated components to get the phrase, "Take 4 10 mg capsules daily." The translated entry is then placed in the pharmacy prescription record. However, if there is no translation which corresponds to one of the predetermined instruction components in the stored list, the system requires manual entry into the pharmacy prescription record.

When there is a translation for the prescriber instructions, the translation may be compared to the days' supply and quantity to make sure a discrepancy does not exist. For example, the days' supply and quantity of the electronic prescription 100 is 30 and 120 respectively, meaning the patient has 120 capsules to take in 30 days. The prescriber instructions indicate taking four capsules a day, and four capsules a day for 30 days amounts to 120 capsules. Therefore, the days' supply and quantity are not at odds with the prescriber instructions. However, when there is a difference, the automated pharmacy processing system may remove the prescriber instructions, quantity, and/or days' supply from the pharmacy prescription record and may require manual entry.

After each of the prescription components have been detected, the automated pharmacy processing system determines whether manual entry is required for any of the prescription components. If manual entry is not required, the pharmacy prescription record is sent to a workstation corresponding to the selected pharmacy location and added to a list of prescriptions for a pharmacist at the selected pharmacy location to fill. On the other hand, if manual entry is required, the pharmacy prescription record is transmitted to a workstation corresponding to the selected pharmacy location for manual entry before it can be filled.

Figure 5A:
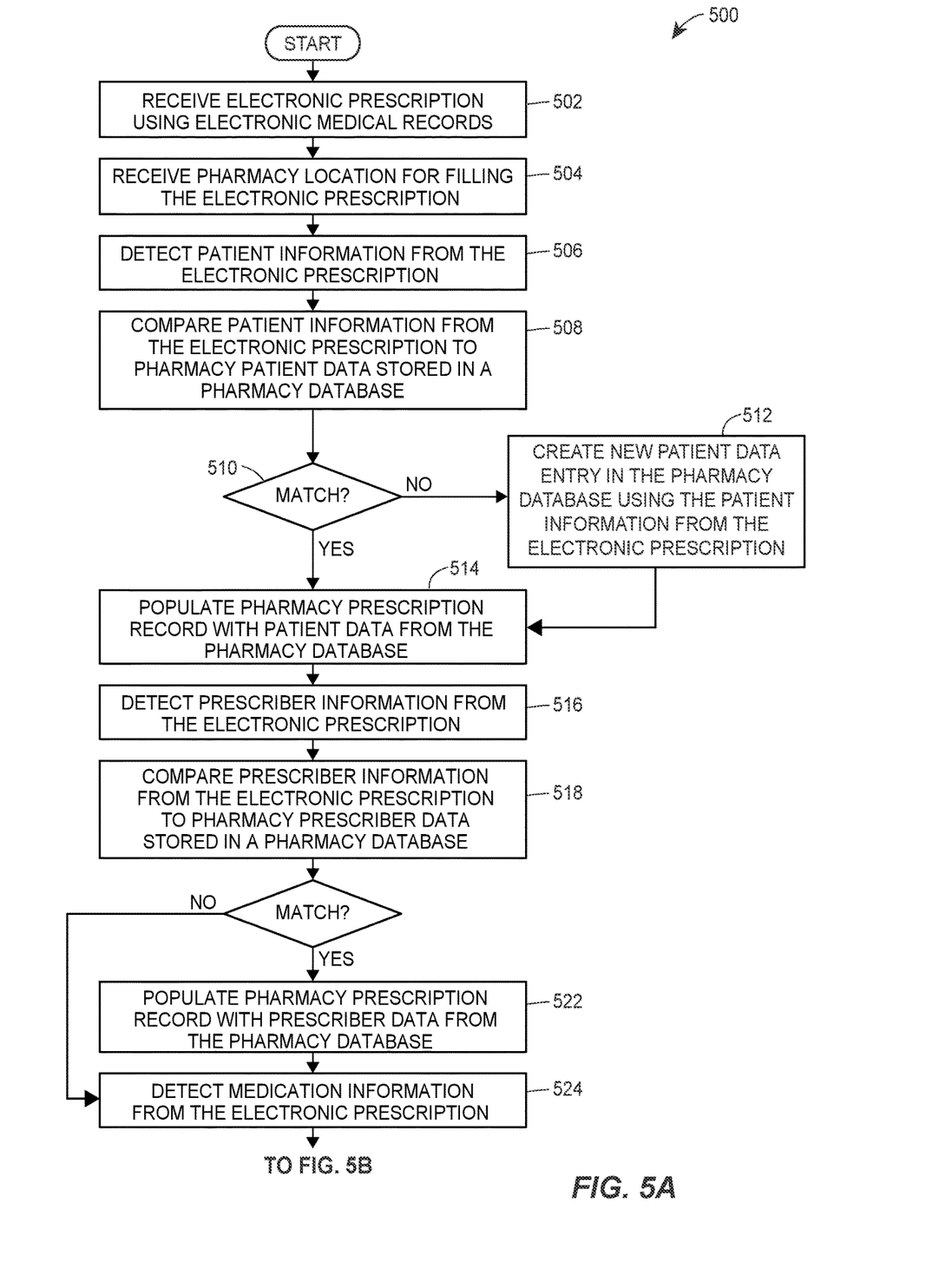
FIG. 5A depicts a flow diagram representing an exemplary method for implementing the automated pharmacy processing system in accordance with the presently described embodiments.
Figure 5B:
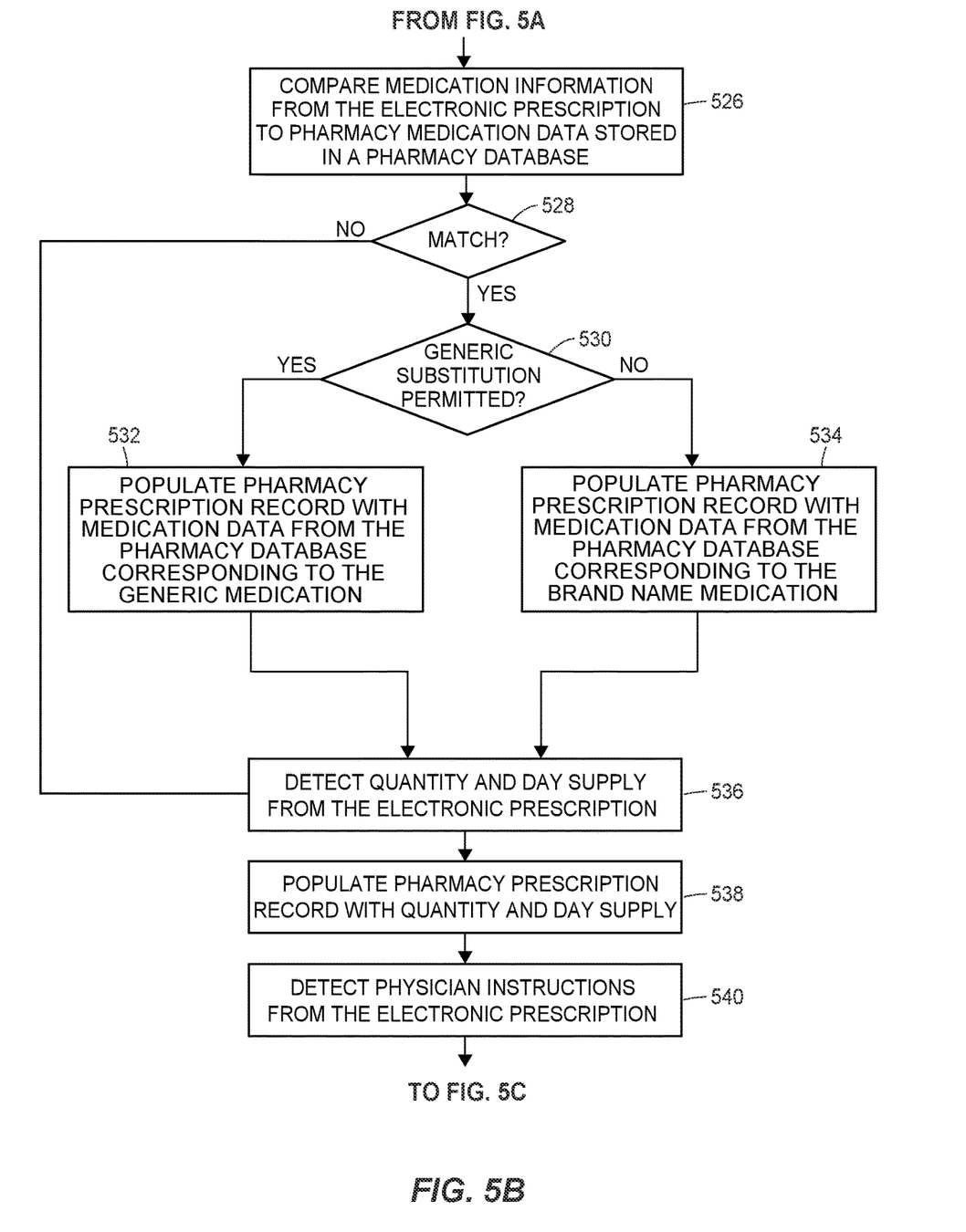
FIG. 5B depicts a flow diagram representing a continuation of the exemplary method in FIG. 5A for implementing the automated pharmacy processing system in accordance with the presently described embodiments.
Figure 5C:
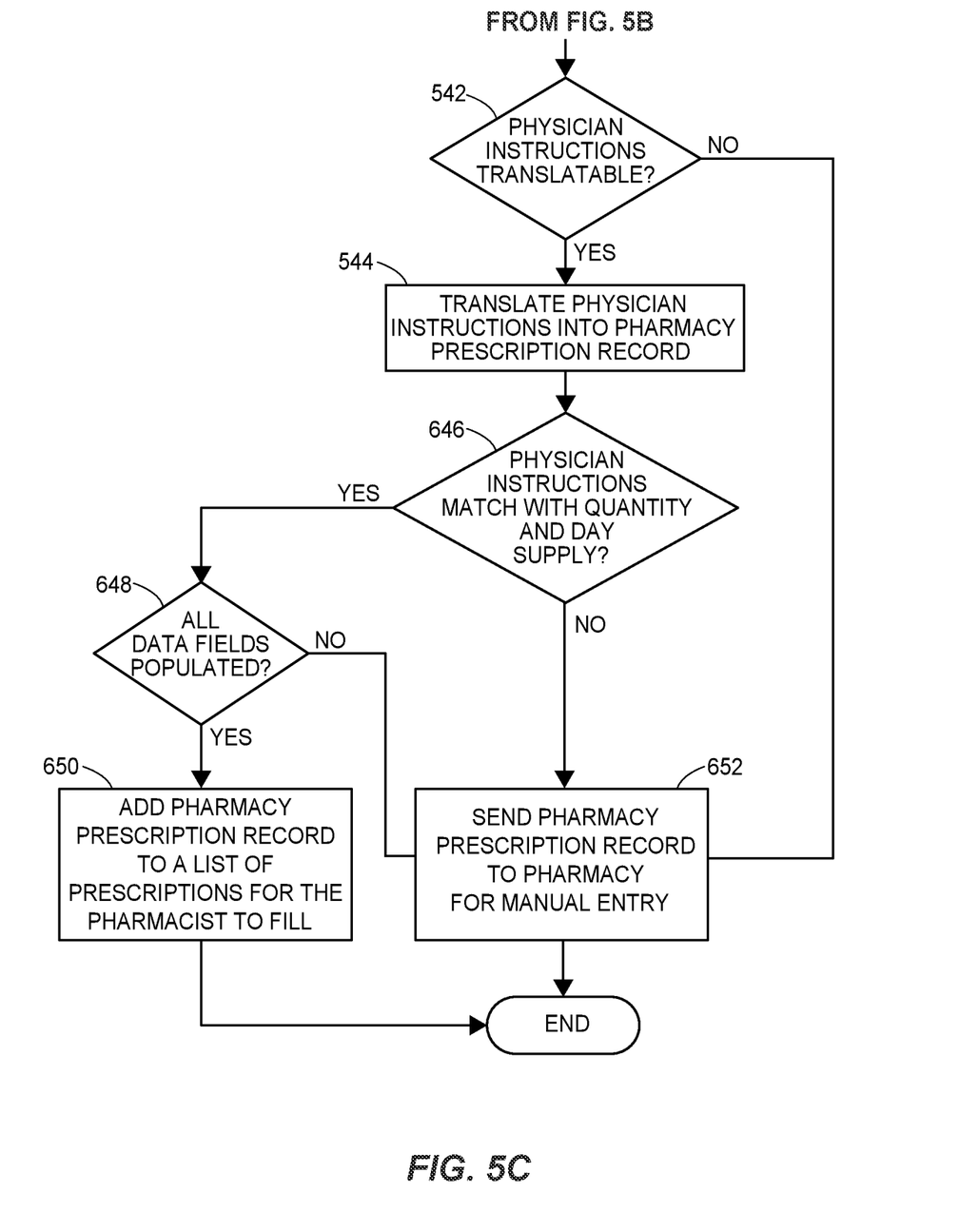
FIG. 5C depicts a flow diagram representing a continuation of the exemplary method in FIG. 5B for implementing the automated pharmacy processing system in accordance with the presently described embodiments.

FIGS. 5A, 5B and 5C depict a flow diagram representing an exemplary method 500 for implementing the automated pharmacy processing system. A prescriber sends electronic prescriptions using electronic medical records (block 502) along with a pharmacy location for filling the electronic prescription (block 504) to the automated pharmacy processing system. The automated pharmacy processing system then detects patient information from the electronic prescription (block 506) and compares this with pharmacy patient data stored in a pharmacy patient database (block 508). If there is a match, the system populates a pharmacy prescription record with patient data from the pharmacy patient database (block 514). Otherwise, the system automatically creates a new patient data entry in the pharmacy patient database using the patient information from the electronic prescription (block 512) and then proceeds to block 514.

Next, the system detects prescriber information from the electronic prescription (block 516) and compares this with pharmacy prescriber data stored in a pharmacy prescriber database (block 518). If there is a match, the system populates a pharmacy prescription record with prescriber data from the pharmacy prescriber database (block 522). Otherwise, the system proceeds to block 524 where medication information from the electronic prescription is detected.

Continuing on to FIG. 5B, the detected medication information from the electronic prescription is compared to pharmacy medication data in a pharmacy medication database (block 526). If there is no match, the system proceeds to block 536. However, if there is a match, the system determines whether generic substitution of a brand name medication is permitted (block 530). This can be determined, for example, by detecting whether a dispense as written field is included in the electronic prescription, or by detecting whether the electronic prescription specifies that generic substitution is allowed. If generic substitution is permitted, the system populates a pharmacy prescription record with medication data from the pharmacy medication database including the generic equivalent of the brand name medication (block 532). In the event there are multiple manufacturers for the generic drug, the automated pharmacy processing system checks the inventory system or modules to determine the exact generic product to dispense. If generic substitution is not permitted, the system alternatively populates a pharmacy prescription record with the brand name medication (block 534).

At block 536, a quantity and days' supply is detected from the electronic prescription and the pharmacy prescription record is populated with the quantity and days' supply (block 538). Then, prescriber instructions from the electronic prescription are detected (block 540).

Moving on to FIG. 5C, if the prescriber instructions can be translated into instructions which have been formatted for the pharmacy prescription record (e.g., instructions which are made up of a set of predetermined prescriber instruction components from the stored list), the instructions are translated and placed in the pharmacy prescription record (block 544), and the system determines whether the instructions are consistent with the quantity and supply (block 546). If the instructions are consistent, the system determines whether each of patient data, prescriber data, medication data, quantity and days' supply, and prescriber instructions have been populated in the pharmacy prescription record. If they all have, the pharmacy prescription record is added to a list of prescriptions for a pharmacist to fill at the selected pharmacy location (block 550). Otherwise, the pharmacy prescription record is transmitted to the pharmacy location for manual data entry (block 552).

Figure 6:
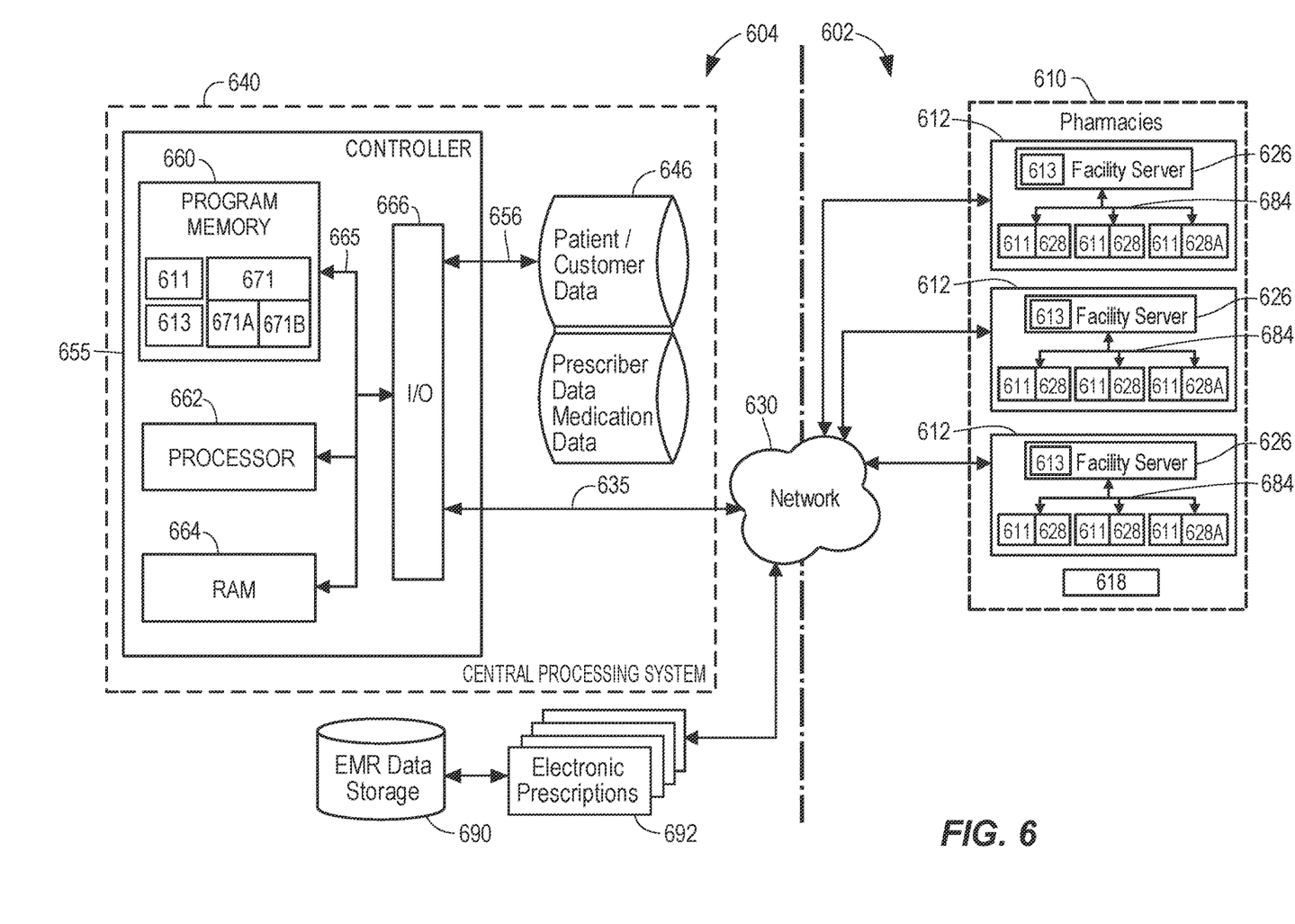
FIG. 6 illustrates a block diagram of a computer network and system on which an exemplary automated pharmacy processing system and method may operate in accordance with the described embodiments.

FIG. 6 illustrates various aspects of an exemplary architecture implementing the automated pharmacy processing system 600. In particular, FIG. 6 illustrates a block diagram of the automated pharmacy processing system 600. The high-level architecture includes both hardware and software applications, as well as various data communications channels for communicating data between the various hardware and software components. The automated pharmacy processing system 600 may be roughly divided into front-end components 602 and back-end components 604. The front-end components 602 are primarily disposed within a retail network 610 including one or more pharmacies 612. The pharmacies 612 may be located, by way of example rather than limitation, in separate geographic locations from each other, including different areas of the same city, different cities, or even different states. The front-end components 602 comprise a number of pharmacy workstations 628. The pharmacy workstations 628 are local computers located in the various pharmacies 612 throughout the retail network 610 and executing various pharmacy management-related applications. Pharmacists, technicians, and other pharmacy personnel, referred to collectively herein simply as "pharmacists" (not shown), use the pharmacy workstations 628 to access customer information, enter new prescriptions, access insurance and payment information and so forth. Each of the pharmacies 612 may be, for example, an in-store retail pharmacy, an on-line pharmacy, a mail-order pharmacy, a long-term care pharmacy, a workplace/on-site pharmacy, or a specialty pharmacy. The retail network 610 may also include one or more warehouses or central-filling facilities 618. The warehouses or central-filling facilities 618 may distribute medications or retail products to the various retail pharmacies 612 in the retail network 610, or may distribute medications or retail products directly to customers.

Those of ordinary skill in the art will recognize that the front-end components 602 could also comprise a plurality of facility servers 626 disposed at the plurality of pharmacies 612 instead of, or in addition to, a plurality of pharmacy workstations 628. Each of the pharmacies 612 may include one or more facility servers 626 that may facilitate communications between the workstations 628 of the pharmacies 612 via a digital network 630, and may store information for a plurality of customers/employees/accounts/etc. associated with each facility. Of course, a local digital network 684 may also operatively connect each of the workstations 628 to the facility server 626. Unless otherwise indicated, any discussion of the workstations 628 also refers to the facility servers 626, and vice versa. Moreover, environments other than the pharmacies 612 may employ the workstations 628 and the servers 626. As used herein, the term "pharmacy" refers to any of these environments (e.g., call centers, kiosks, Internet interface terminals, etc.) in addition to the retail pharmacies 612, etc. described above.

The front-end components 602 communicate with the back-end components 604 via the digital network 630. One or more of the front-end components 602 may be excluded from communication with the back-end components 604 by configuration or by limiting access due to security concerns. In some embodiments, the pharmacies 612 may communicate with the back-end components via the digital network 630. In other embodiments, the pharmacies 612 may communicate with the back-end components 604 via the same digital network 630.

Additionally, electronic prescriptions 692 may be transmitted in the form of electronic data files from an EMR data storage entity 690 to the automated pharmacy processing system 600 via the digital network 630. Alternatively, electronic prescriptions 692 may be transmitted from an EHR data storage entity (not shown) or a standalone e-Prescribing data storage entity (not shown). An electronic prescription 692 corresponding to a particular patient may be an electronic data file and may be used in lieu of or in addition to standard paper prescriptions. Information or data stored in an electronic prescription 692 may include, for example, the patient name, the patient address, the patient birth date, the prescriber name, the prescriber license number, the medication name, the quantity, a days' supply, specific instructions from the prescriber, etc. Privacy of patients' EMRs may be privacy protected according to local and/or federal government laws and regulations. The EMR data storage entity 690 may include one or more data storage devices of any known non-transitory, tangible, computer-readable storage media technology, e.g., disks, solid state devices, data banks, servers, cloud storage, etc. The central processing system 640 or the facility servers 626 may receive the electronic prescriptions 692 via the digital network 630.

The digital network 630 may be a proprietary network, a secure public Internet, a virtual private network or some other type of network, such as dedicated access lines, plain ordinary telephone lines, satellite links, combinations of these, etc. Where the digital network 630 comprises the Internet, data communication may take place over the digital network 630 via an Internet communication protocol. The back-end components 604 include the central processing system 640 within a central processing facility, such as, for example, the central processing facility described in U.S. Pat. No. 8,175,891 entitled "DISTRIBUTED PHARMACY PRESCRIPTION PROCESSING SYSTEM" the entire disclosure of which is incorporated by reference herein. Of course, the pharmacies 612 may be communicatively connected to different back-end components 604 having one or more functions or capabilities that are similar to the central processing system 640. The central processing system 640 may include one or more computer processors 662 adapted and configured to execute various software applications and components of the new prescription order system 600, in addition to other software applications.

The central processing system 640 further includes a database 646. The database 646 is adapted to store data related to the operation of the automated pharmacy processing system 600 (e.g., patient profile data, physician profile data as well as medication data, etc.). In some embodiments, the database 646 may include the pharmacy patient database 200, the pharmacy prescriber database 300 and the pharmacy medication database 400, as shown in FIGS. 2-4. The central processing system 640 may access data stored in the database 646 when executing various functions and tasks associated with the operation of the new prescription order system 600. For simplicity, FIG. 6 illustrates the database 646 as only one instance of a database. However, the database 646 according to some implementations includes a group of one or more databases, each storing different information. For example, one database may store patient profile data while another may store physician profile data. For the purposes of this discussion, the term "database" 646 may refer to an individual database or to a group of two or more databases.

Although FIG. 6 depicts the automated pharmacy processing system 600 as including the central processing system 640 in communication with three pharmacies 612, it should be understood that different numbers of processing systems and pharmacies may be utilized. For example, the digital network 630 (or other digital networks, not shown) may interconnect the central processing system 640 to a plurality of included central processing systems 640 and hundreds of pharmacies 612. According to the disclosed example, this configuration may provide several advantages, such as, for example, enabling near real-time uploads and downloads of information as well as periodic uploads and downloads of information. This provides for a primary backup of all the information generated in the automated pharmacy process. Alternatively, some of the pharmacies 612 may store data locally on the facility server 626 and/or the workstations 628.

FIG. 6 also depicts one possible embodiment of the central processing system 640. The central processing system 640 may have a controller 655 operatively connected to the database 646 via a link 656 connected to an input/output (I/O) circuit 666. It should be noted that, while not shown, additional databases may be linked to the controller 655 in a known manner.

The controller 655 includes a program memory 660, the processor 662 (may be called a microcontroller or a microprocessor), a random-access memory (RAM) 664, and the input/output (I/O) circuit 666, all of which are interconnected via an address/data bus 665. It should be appreciated that although only one microprocessor 662 is shown, the controller 655 may include multiple microprocessors 662. Similarly, the memory of the controller 655 may include multiple RAMs 664 and multiple program memories 660. Although the I/O circuit 666 is shown as a single block, it should be appreciated that the I/O circuit 666 may include a number of different types of I/O circuits. The RAM(s) 664 and the program memories 660 may be implemented as semiconductor memories, magnetically readable memories, and/or optically readable memories, for example. A link 635 may operatively connect the controller 655 to the digital network 630 through the I/O circuit 666.

The program memory 660 may also contain machine-readable instructions (i.e., software) 671, for execution by the processor 662. The software 671 may perform the various tasks associated with operation of the pharmacy or pharmacies, and may be a single module 671 or a plurality of modules 671A, 671B. While the software 671 is depicted in FIG. 6 as including two modules, 671A and 671B, the software 671 may include any number of modules accomplishing tasks related to pharmacy operation including, for example, receiving prescription orders, managing prescription workflow, etc. In some embodiments, the software 671 may include instructions for implementing the exemplary method 500 as shown in FIGS. 5A-C. The central processing system 640 implements a server application 613 for providing data to a user interface application 611 operating on the workstations 628.

As described above, the database 646, illustrated in FIG. 6, includes various information about the pharmacy's customers, prescribing physicians, and prescription medications. Customer records are among the exemplary data that the automated pharmacy processing system 600 may store on the database 646. A customer record contains important information about the customer and the various pharmacy services that have been invoked by, or on behalf of, the customer in a customer profile. The customer profile includes basic biographical information about the customer, such as a customer name, a customer social security number, a customer address, a customer phone number, a customer birth date, customer prescription history, customer allergies, customer insurance information etc. Prescribing physician records may also be stored on the database 646. Prescribing physician records may include a prescriber name, a practice name, a prescriber DEA number, a prescriber phone number, a prescriber office address, etc. The database 646 may also store a list of predetermined prescriber instruction components. Moreover, prescription medication records may include a medication name, a size of the medication, a generic equivalent, whether the medication is a controlled substance, a Dispense as Written (DAW) code, a National Drug Code (NDC), etc.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer implemented method for converting an electronic prescription into a pharmacy prescription, the method comprising:
   receiving, via one or more processors of a pharmacy processing system at a pharmacy, electronic prescription data from a healthcare provider,
   wherein the electronic prescription data is representative of an electronic prescription, and includes a dosage component, a frequency component, a number of days supplied and a total quantity;
   transforming, by the pharmacy processing system, individual components of the electronic prescription into respective prescriber components based on a comparison of identified individual components of the electronic prescription with a list of predetermined prescriber components,
      wherein the transforming includes (i) translating the dosage component to a translated dosage component and (ii) translating the frequency component to a translated frequency component; and
   generating, via one or more processors, prescriber data based on the prescriber components, wherein the prescriber data is representative of a pharmacy prescription.

2. The method of claim 1, further comprising:
   combining the translated dosage component and the translated frequency component to a combined component;
   multiplying the translated dosage component by the translated frequency component to derive a calculated component; and
   entering the combined component and the calculated component in a pharmacy prescription record.

3. The method of claim 1, further comprising:
   combining the translated dosage component and the translated frequency component to a combined component;
   dividing the total quantity by the number of days supplied to derive a calculated component; and
   comparing the combined component to the calculated component, when the one or more processors determine a difference between the combined component and the calculated component, the one or more processors remove the total quantity and the number of days supplied from the pharmacy prescription record and transmits the pharmacy prescription record to a workstation corresponding to a selected pharmacy location for manual entry before an associated prescription is filled.

4. The method of claim 1, further comprising:
   determining whether a generic medication substitution is permitted for a prescription, and when generic medication substitution is permitted, modifying the pharmacy prescription record utilizing information corresponding to the generic medication substitution.

5. The method of claim 1, further comprising:
   comparing patient identification information from the electronic prescription to a stored list of registered patients in a database, wherein comparing the patient identification information from the electronic prescription to a stored list of registered patients in a database comprises, when there is no match, adding a patient data entry to the stored list based on the patient identification information from the electronic prescription.

6. The method of claim 5, wherein the patient identification information includes at least one of: a patient name, a patient phone number, a patient address, a patient birth date, patient prescription history, allergies, or patient insurance information.

7. The method of claim 1, further comprising:
   receiving physician identification information, wherein the physician identification information includes at least one: of a physician name, a practice name, a physician phone number, a physician address, or a DEA number.

8. A pharmacy processing system at a pharmacy for converting an electronic prescription into a pharmacy prescription, the pharmacy processing system comprising:
   one or more processors; and
   a non-transitory computer-readable memory coupled to the one or more processors and storing instructions thereon that, when executed by the one or more processors, cause the system to:
   receive, via one or more processors, electronic prescription data from a healthcare provider,
   wherein the electronic prescription data is representative of an electronic prescription, and includes a dosage component, a frequency component, a number of days supplied and a total quantity;
   transform, via one or more processors, by the pharmacy processing system, individual components of the electronic prescription into respective prescriber components based on a comparison of identified individual components of the electronic prescription with a list of predetermined prescriber components, by translating the dosage component to a translated dosage component and translating the frequency component to a translated frequency component; and generate, via one or more processors, prescriber data based on the prescriber components, wherein the prescriber data is representative of a pharmacy prescription.

9. The system of claim 8, wherein the one or more processors are further configured to:

combine, via the one or more processors, the translated dosage component and the translated frequency component to a combined component;

multiply the translated dosage component by the translated frequency component to derive a calculated component; and enter, via the one or more processors, the combined component and the calculated component in a pharmacy prescription record.

10. The system of claim 8, wherein the one or more processors are further configured to:

combine, via the one or more processors, the translated dosage component and the translated frequency component to a combined component;

divide, via the one or more processors, the total quantity by the number of days supplied to derive a calculated component;

compare, via the one or more processors, the combined component to the calculated component; and when the one or more processors determines a difference between the combined component and the calculated component, the one or more processors removes the total quantity and the number of days supplied from the pharmacy prescription record and transmits the pharmacy prescription record to a workstation corresponding to a selected pharmacy location for manual entry before an associated prescription is filled.

11. The system of claim 8, wherein the one or more processors are further configured to:

determine whether a generic medication substitution is permitted for a prescription, and when generic medication substitution is permitted, modifying the pharmacy prescription record utilizing information corresponding to the generic medication substitution.

12. The system of claim 8, wherein the one or more processors are further configured to:

compare patient identification information from the electronic prescription to a stored list of registered patients in a database, wherein comparing the patient identification information from the electronic prescription to a stored list of registered patients in a database comprises, when there is no match, adding a patient data entry to the stored list based on the patient identification information from the electronic prescription.

13. The system of claim 8, wherein the one or more processors are further configured to:

receive physician identification information, wherein the physician identification information includes at least one: of a physician name, a practice name, a physician phone number, a physician address, or a DEA number.

14. A non-transitory, computer-readable medium storing instructions that, when executed by one or more processors, cause a computer to:

receive, via one or more processors of a pharmacy processing system at a pharmacy, electronic prescription data from a healthcare provider, wherein the electronic prescription data is representative of an electronic prescription, and includes a dosage component, a frequency component, a number of days supplied and a total quantity;

transform, via one or more processors, by the pharmacy processing system, individual components of the electronic prescription into respective prescriber components based on a comparison of identified individual components of the electronic prescription with a list of predetermined prescriber components by translating the dosage component to a translated dosage component and translating the frequency component to a translated frequency component, and generate, via one or more processors, prescriber data based on the prescriber components, wherein the prescriber data is representative of a pharmacy prescription.

15. The non-transitory computer-readable medium of claim 14, wherein execution of the instructions by the one or more processors, cause a computer to:

combine the translated dosage component and the translated frequency component to a combined component;

multiply the translated dosage component by the translated frequency component to derive a calculated component; and enter the combined component and the calculated component in a pharmacy prescription record.

16. The non-transitory computer-readable medium of claim 14, wherein execution of the instructions by the one or more processors, cause a computer to:

combine the translated dosage component and the translated frequency component to a combined component;

divide the total quantity by the number of days supplied to derive a calculated component; and compare the combined component to the calculated component, when the processor determines a difference between the combined component and the calculated component, the processor removes the total quantity and the number of days supplied from the pharmacy prescription record and transmits the pharmacy prescription record to a workstation corresponding to a selected pharmacy location for manual entry before an associated prescription is filled.

17. The non-transitory computer-readable medium of claim 14, wherein execution of the instructions by the one or more processors, cause a computer to:

determine whether a generic medication substitution is permitted for a prescription, and when generic medication substitution is permitted, causes the processor to modify the pharmacy prescription record utilizing information based on the generic medication substitution.

18. The non-transitory computer-readable medium of claim 14, wherein execution of the instructions by the one or more processors, cause a computer to:

compare patient identification information from the electronic prescription to a stored list of registered patients in a database, wherein comparing the patient identification information from the electronic prescription to a stored list of registered patients in a database comprises, when there is no match, causes the processor to add a patient data entry to the stored list based on the patient identification information from the electronic prescription.

19. The non-transitory computer-readable medium of claim 18, wherein the patient identification information includes at least one of:
a patient name, a patient phone number, a patient address, a patient birth date, patient prescription history, allergies, or patient insurance information.

20. The non-transitory computer-readable medium of claim 18, wherein execution of the instructions by the one or more processors, cause a computer to:
receive physician identification information, wherein the physician identification information includes at least one: of a physician name, a practice name, a physician phone number, a physician address, or a DEA number.

* * * * *